US009759903B2

(12) United States Patent
Buerk et al.

(10) Patent No.: US 9,759,903 B2
(45) Date of Patent: Sep. 12, 2017

(54) DRYING AGENT ARRANGEMENT FOR OPTICAL INSTRUMENTS

(75) Inventors: Andre Buerk, Villingen-Schwenningen (DE); Michael Egle, Boettingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 1064 days.

(21) Appl. No.: 13/461,966

(22) Filed: May 2, 2012

(65) Prior Publication Data

US 2012/0283515 A1  Nov. 8, 2012

(30) Foreign Application Priority Data

May 2, 2011  (DE) .................... 10 2011 100 232

(51) Int. Cl.
| | |
|---|---|
| A61B 1/04 | (2006.01) |
| A61B 1/06 | (2006.01) |
| A61B 1/12 | (2006.01) |
| G02B 23/24 | (2006.01) |
| A61B 1/00 | (2006.01) |

(52) U.S. Cl.
CPC ...... *G02B 23/2476* (2013.01); *A61B 1/00066* (2013.01); *A61B 1/00137* (2013.01); *A61B 1/00142* (2013.01); *A61B 1/00195* (2013.01); *A61B 1/127* (2013.01)

(58) Field of Classification Search
CPC ................................ A61B 1/126; A61B 1/127
USPC ................. 600/129, 133, 155–157, 175–176
See application file for complete search history.

(56) References Cited

U.S. PATENT DOCUMENTS

| | | | |
|---|---|---|---|
| 6,077,220 A | 6/2000 | Rudischhauser et al. | |
| 2010/0174144 A1* | 7/2010 | Hsu et al. ..................... | 600/122 |

FOREIGN PATENT DOCUMENTS

| | | |
|---|---|---|
| DE | 2128428 A1 | 1/1973 |
| DE | 3708124 A1 | 9/1987 |
| DE | 19507205 A1 | 11/1995 |
| DE | 19940844 A1 | 3/2000 |
| DE | 10344109 A1 | 4/2005 |

(Continued)

OTHER PUBLICATIONS

European Search Report; Application No. EP 12 00 2769; Issued: Jul. 6, 2012; 6 pages.

(Continued)

*Primary Examiner* — Ryan Henderson
(74) *Attorney, Agent, or Firm* — Whitmyer IP Group LLC

(57) ABSTRACT

A drying agent arrangement for optical instruments, in particular for endoscopic instruments, having a hygroscopic substance in the instrument housing, such that the hygroscopic substance, configured as individual molded bodies, is positioned in an intake receptacle that can be replaceably inserted in the instrument housing. To provide a drying agent arrangement that, along with simple, versatile application, allows the intake of a great quantity of drying agent, the intake receptacle may be configured as a double-walled sleeve, such that the two walls, forming an intake space for the molded bodies of the hygroscopic substance, are radially distanced from one another and positioned in such a way that the walls, closing the intake space at one axial end of the sleeve, are connected with one another at the end and on the other axial end of the sleeve, releasing the intake space, are radially distanced from one another at the end.

10 Claims, 3 Drawing Sheets

(56) References Cited

FOREIGN PATENT DOCUMENTS

| | | |
|---|---|---|
| DE | 102004045395 A1 | 3/2006 |
| EP | 0916106 A1 | 5/1999 |
| GB | 1502445 A | 3/1978 |
| JP | 2004073259 A | 3/2004 |
| WO | PCT/US08/06923 | * 12/2008 |

OTHER PUBLICATIONS

German Search Report; Application No. DE 10 2011 100 232.8; Issued: Jan. 13, 2012; 5 pages.

* cited by examiner

DRYING AGENT ARRANGEMENT FOR OPTICAL INSTRUMENTS

CROSS-REFERENCE TO RELATED APPLICATIONS

The present application claims priority of German patent application No. 10 2011 100 232.8 filed on May 2, 2011.

FIELD OF THE INVENTION

The invention relates to a drying agent arrangement for optical instruments, in particular for endoscopic instruments, having a hygroscopic substance installed in the instrument housing, such that the hygroscopic substance configured as individual moulded bodies is positioned in an intake receptacle that can be replaceably inserted in the instrument housing.

BACKGROUND OF THE INVENTION

Optical instruments and in particular endoscopic instruments for medical and non-medical purposes are in general fluid-tight systems. For a series of reasons, however, there is the possibility that moisture can penetrate the housing, which can result in misting of the optical systems that restricts the view. Problems can arise, for example, even during manufacture of the optical instruments in normal atmosphere, if the moisture residue of the atmospheric air precipitates inside the housing. In addition, moisture can penetrate through minor leaks at connecting points at which the instrument can be taken apart for purposes of maintenance, repair or assembly. An additional strong impact, in particular of medical optical instruments, is constituted by cleaning by means of autoclaving, in which the instrument under variable pressure is exposed to superheated steam at approximately 140 degrees C. This temperature impact can result in minute leaks which, again, can allow moisture to penetrate the housing.

To avoid misting problems of this type from moisture precipitating on the optical system, a known method with optical instruments is to install a hygroscopic substance in the housing that binds the moisture accumulating in the housing internal space before it precipitates on the at least one optical system.

Thus it is a known practice, for example, to install the hygroscopic substance in the housing in loose form. This has the disadvantage, however, that in moving the instrument, noises occur and in addition, owing to the movement, abrasion of the hygroscopic substance is generated that can settle on the optical systems as dust.

Another known practice, from EP 0 916 106 B1, is to install the hygroscopic substance in the form of prefabricated moulded bodies, such as spheres or small rods for example, in a recess in the eyecup and to place it in stationary manner in this recess by means of a fixer element.

This known drying agent arrangement has proven itself completely in the art, but the arrangement of the hygroscopic substance in a housing recess allows use of only a small quantity of drying agent and in addition requires a special configuration of the eyecup.

A generic drying agent arrangement is known, for example, from DE 103 44 109 A1. With this known arrangement, the hygroscopic substance can be configured, for example, in spherical form, such that these spherical moulded shapes are disposed in a cage for stationary fastening.

SUMMARY OF THE INVENTION

Consequently it is an object of the invention to provide a drying agent arrangement that, along with simple, versatile application, allows the intake of a great quantity of drying agent.

This object is fulfilled according to the invention in a manner characterized in that the intake receptacle is configured as a double-walled sleeve, such that the two walls, forming an intake space for the moulded bodies of the hygroscopic substance, are distanced radially from one another and disposed in such a way that the walls, closing the intake space at one axial end of the sleeve, are connected at the end with one another and, at the other axial end of the sleeve, releasing the intake space, are radially distanced from one another at the end.

As a result of the inventive arrangement of the hygroscopic substance in an intake receptacle that can be replaceably inserted in the instrument housing, it is possible to manufacture and equip the drying agent arrangement, which comprises an intake receptacle and hygroscopic substance, as an independent structural unit in order to place this finished structural unit in the instrument housing in a single assembly step.

Owing to the configuration, open on one side, of the intake space for the moulded bodies of the hygroscopic substance configured preferably as spheres or small rods, an arrangement for the drying agent is provided that comprises a simple structure, comprising only of a few structural elements, and that allows easy intake of any moisture possibly penetrating the instrument housing.

To increase the hygroscopic effect of the drying agent arrangement, the moulded bodies of the hygroscopic substance may be mountable in several layers in the intake receptacle in axial direction, so that assembly is simple and a great number of moulded bodies of the hygroscopic substance can be placed in the intake receptacle.

It is further disclosed that for the intake of hygroscopic substance in the intake space, separate, radially surrounding intake shafts for the moulded bodies of the hygroscopic substance may be configured that extend in the axial direction and in which the moulded bodies of the hygroscopic substance are arranged at a radial distance from one another. This configuration of the individual intake shafts in the intake receptacle, on the one hand, allows a simple and always uniform application of the hygroscopic substance on the intake receptacle and, on the other hand, prevents the occurrence of a relative movement in the radial direction between the moulded bodies, which could lead in turn to abrasion that forms a dust.

To retain the moulded bodies of the hygroscopic substance in stationary manner in the intake receptacle, the moulded bodies of the hygroscopic substance may be capable of being secured in the intake receptacle by means of a fixer element, preferably an O-ring.

According to a practical embodiment of the invention, there may be configured in the intake receptacle a radially surrounding groove for intake of the fixer element, by which the fixer element can be secured on the intake receptacle easily and quickly.

The inside of the sleeve may be configured by coloring, coating and/or surface structuring in such a way that the occurrence of scattered light can be kept low. To configure a surface structuring that minimizes scattered light, fluting with tips should preferably be configured on the inside of the sleeve.

Further features and advantages of the invention can be seen from the related drawings, in which an embodiment of an inventive drying agent arrangement for optical instruments is illustrated only by way of example, without restricting the invention to this embodiment.

DETAILED DESCRIPTION OF THE INVENTION

Figure 1:
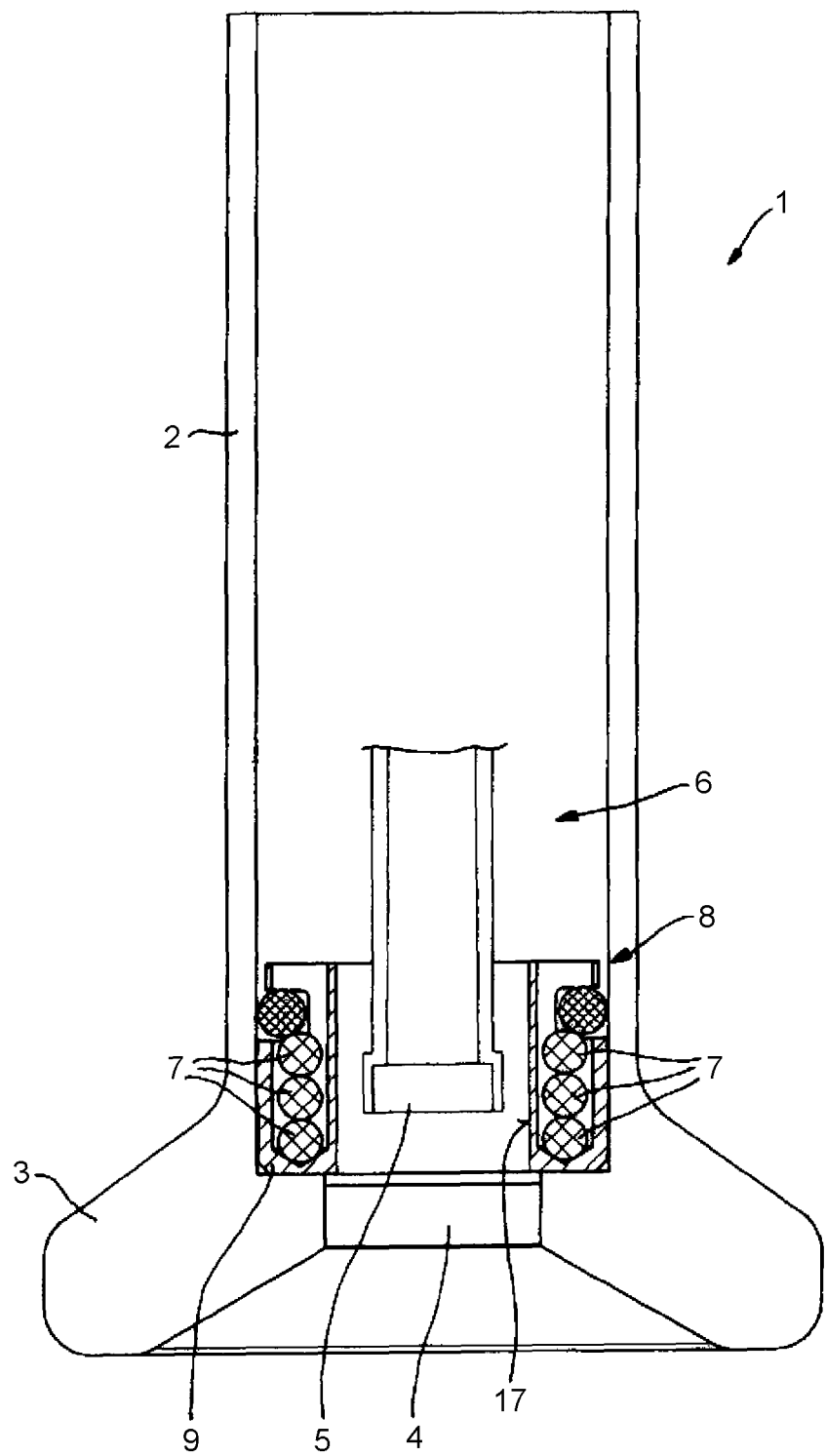
FIG. 1 shows a longitudinal section through the eyepiece unit of an optical instrument with an inventive drying agent arrangement.

The illustration in FIG. 1 shows an eyepiece unit 1 of an optical instrument, such as an endoscope for medical and non-medical purposes, for example. The illustrated eyepiece unit 1 comprises an eyecup sleeve 2 with a one-piece shaped eyecup 3 on the proximal side as well as an eyepiece cover glass 4, which for example is cemented into the eyecup 3 and closes off the eyepiece unit 1 on the proximal side so that it is fluid-tight. Positioned in the interior of the eyepiece unit 1 is an optical system 6 that comprises at least one lens 5. On the distal side the eyecup sleeve 2, which forms a part of the instrument housing 2, is screwed on fluid-tight with the non-illustrated remaining instrument housing of the endoscope or other optical instrument.

Alternatively to the illustrated one-piece configuration of the eyecup 3 and eyecup sleeve 2, it is also possible of course to configure the eyecup 3 and the eyecup sleeve 2 as separate components that can be connected with one another, for example by screw-on connection.

To remove any moisture residue possibly present in the instrument housing 2, as well as for intake of moisture that has penetrated into the instrument housing 2 by way of leaks, a drying agent arrangement 8, equipped with a hygroscopic substance 7, is mounted inside the instrument housing 2. Synthetic zeolites or other clay minerals, for example, or else silica gels are used as materials for producing the hygroscopic substance 7.

The drying agent arrangement 8 shown in FIGS. 1 through 4 comprises an intake receptacle 9 that can be replaceably inserted in the eyecup sleeve 2 and in which the hygroscopic substance 7 configured as moulded bodies is installed. In the illustrated embodiment, the moulded bodies of the hygroscopic substance 7 are configures as spheres. The moulded bodies of the hygroscopic substance 7 can likewise be configured in rod shape.

Figure 2:
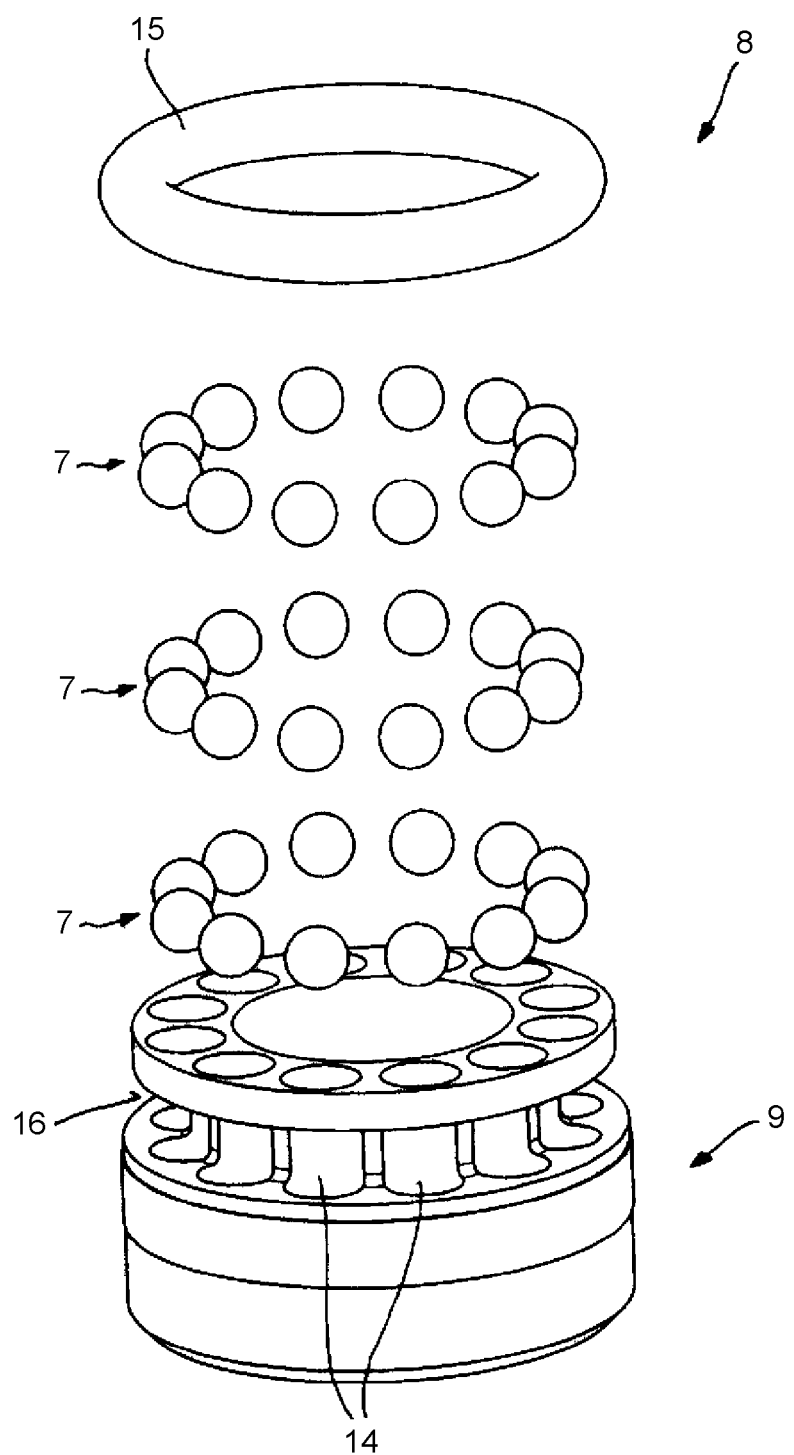
FIG. 2 shows an explosion drawing of the drying agent arrangement according to FIG. 1.
Figure 3:
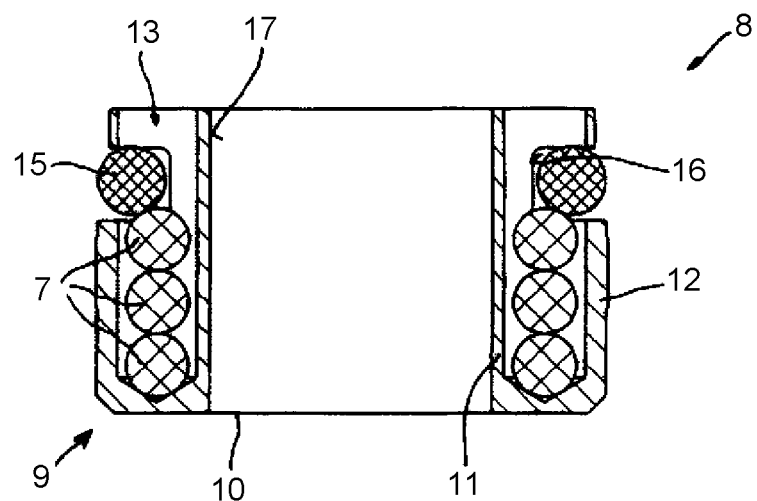
FIG. 3 shows a longitudinal section through the drying agent arrangement according to FIG. 2 in assembled condition.
Figure 4:
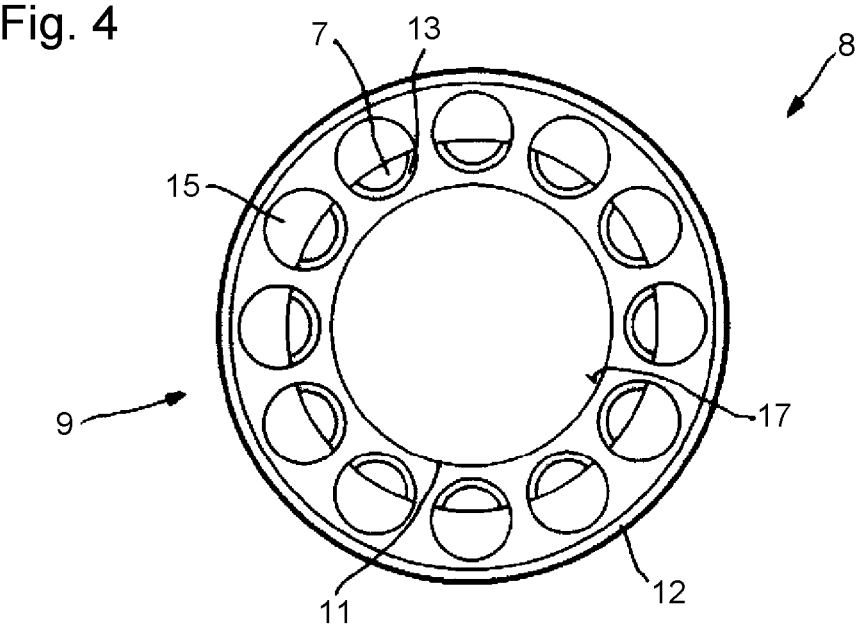
FIG. 4 shows an overhead view of the drying agent arrangement according to FIG. 3.

The structure of the drying agent arrangement 8 can be seen in particular in the images in FIGS. 2 through 4.

As can be seen in particular from FIG. 3, the intake receptacle 9 is configured as a double-walled sleeve 10, such that the two walls 11 and 12 of the double-walled sleeve 10, forming an intake space 13 for the moulded bodies of the hygroscopic substance 7, are positioned at a distance radially from one another and coaxially to one another. The sleeve 10 is configured in such a way that the walls 11 and 12 are connected with one another at the end, closing the intake space 13 at one axial end of the sleeve 10, while at the other axial end of the sleeve 10, releasing the intake space 13, they are at a distance radially from one another at the end.

In the intake space 13 that serves to receive the hygroscopic substance 7, separate, radially surrounding intake shafts 14 for the moulded bodies of the hygroscopic substance 7 are configured that extend in the axial direction and in which the moulded bodies of the hygroscopic substance 7 are positioned, at a distance radially from one another. This configuration of the individual intake shafts 14 in the intake receptacle 13, on the one hand, allows a simple and always uniform equipping of the intake receptacle 9 with the hygroscopic substance 7 and, on the other hand, prevents the occurrence in the radial direction of a relative movement between the moulded bodies, which in turn could lead to abrasion that forms a dust.

In the illustrated embodiment of the intake receptacle 9, three layers, each with twelve spherical moulded bodies of the hygroscopic substance 7, can be installed in the intake shafts 14 of the intake receptacle 9.

To secure the moulded bodies of the hygroscopic substance 7 in stationary manner in the intake receptacle 9, a fixer element 15, preferably configured as an O-ring, can be installed in a radially surrounding groove 16 configured in the intake receptacle 9. In the illustrated embodiment, the radially surrounding groove 16 is configured and disposed in the radially outer wall 12 of the sleeve 10 in such a way that the fixer element 15 inserted into the groove 16 and preferably configured as an O-ring, in assembled state concludes in the radial direction toward the outside essentially flush with the outside of the wall 12 of the sleeve 10, and in the radial direction toward the inside covers approximately only half of the radial depth of the intake shafts 14, in order to ensure, along with a secure grip, the greatest possible free access to the hygroscopic substance.

In the axial direction the groove 16 is configured in the wall 12 of the sleeve 10 in such a way that the fixer element 15 inserted into the groove 16 in assembled state is contiguous with the topmost moulded body of the hygroscopic substance 7, in order thereby to fix the individual moulded bodies of the hygroscopic substance 7, which are positioned in the intake shafts 14, in the axial direction with respect to one another.

As a result of the arrangement of the hygroscopic substance 7 in the intake receptacle 9 that can be inserted replaceably in the instrument housing 2, it is possible to manufacture and equip the drying agent arrangement 8, comprising an intake receptacle 9 and hygroscopic substance 7, as an independent structural unit in order to place this ready-made structural unit in the instrument housing 2 in a single assembly step, for example by pressing it in.

The configuration of the separate intake receptacle 9 has the additional advantage that the length of the eyecup sleeve 2 can be freely selected, since it requires no adaptation of the eyecup sleeve 2 to the intake receptacle 9. Moreover, the structure of the intake receptacle 9 ensures that the hygroscopic substance 7 cannot be moistened by any other medium and the open structure guarantees good intake of any possible moisture penetrating into the eyecup sleeve 2 by the hygroscopic substance installed in the intake receptacle 9.

To be able to keep the occurrence of scattered light in the inside of the eyecup sleeve 2 as low as possible, the inside 17 of the sleeve 10 can be configured by coloring, coating and/or surface structuring in such a way that the risk of adverse effects on the optical system 6 is minimized. To configure a surface structuring that minimizes scattered light, fluting can be configured, preferably with tips, on the inside 17 of the sleeve 10.

The invention claimed is:

1. A drying agent arrangement for optical instruments, having a hygroscopic substance installed inside an instrument housing of the optical instrument, such that the hygroscopic substance, configured as individual moulded bodies, is installed in an intake receptacle that can be replaceably inserted in the instrument housing, characterized in that the intake receptacle is configured as a double-walled sleeve, such that the two walls, forming an intake space for the moulded bodies of the hygroscopic substance, are distanced radially from one another and positioned so that the walls, closing the intake space at an axial end of the sleeve, are connected with one another at the end, and at the other axial end of the sleeve, releasing the intake space, are distanced radially from one another at the end.

2. The drying agent arrangement according to claim 1, wherein the moulded bodies of the hygroscopic substance can be mounted in several layers in the intake receptacle in axial direction.

3. The drying agent arrangement according to claim 1, wherein in the intake space, separate, radially surrounding intake shafts, extending in the axial direction, are configured for the moulded bodies of the hygroscopic substance.

4. The drying agent arrangement according to claim 3, wherein the moulded bodies of the hygroscopic substance are positioned radially at a distance from one another in the intake shafts of the intake space.

5. The drying agent arrangement according to claim 1, wherein the moulded bodies of the hygroscopic substance can be secured in the intake receptacle by a fixer element, preferably an O-ring.

6. The drying agent arrangement according to claim 5, wherein in the intake receptacle a radially surrounding groove is configured for intake of the fixer element.

7. The drying agent arrangement according to claim 1, wherein the moulded bodies of the hygroscopic substance are configured as spheres or small rods.

8. The drying agent arrangement according to claim 1, wherein the inside of the sleeve is equipped to minimize scattered light by coloring, coating and/or surface structuring.

9. The drying agent arrangement according to claim 5, wherein on the inside of the sleeve, fluting is configured to provide a surface structure that minimizes scattered light.

10. The drying agent arrangement according to claim 1, wherein the optical instruments are endoscopic instruments.

\* \* \* \* \*